US011234928B2

(12) United States Patent
Minato et al.

(10) Patent No.: US 11,234,928 B2
(45) Date of Patent: Feb. 1, 2022

(54) POWDER PREPARATION FOR NASAL ADMINISTRATION

(71) Applicant: ASKA Pharmaceutical Co., Ltd., Tokyo (JP)

(72) Inventors: Koichi Minato, Kanagawa (JP); Tomoya Fujisawa, Kanagawa (JP); Kenji Shimizu, Kanagawa (JP); Takahisa Saito, Kanagawa (JP); Hiroya Yajima, Kanagawa (JP); Kazuhiro Sasaki, Kanagawa (JP)

(73) Assignee: ASKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/760,075

(22) PCT Filed: Nov. 22, 2018

(86) PCT No.: PCT/JP2018/043233
§ 371 (c)(1),
(2) Date: Apr. 29, 2020

(87) PCT Pub. No.: WO2019/103108
PCT Pub. Date: May 31, 2019

(65) Prior Publication Data
US 2020/0360274 A1 Nov. 19, 2020

(30) Foreign Application Priority Data
Nov. 27, 2017 (JP) .............................. JP2017-227133

(51) Int. Cl.
*A61K 9/00* (2006.01)
*A61K 31/568* (2006.01)
*A61K 47/38* (2006.01)

(52) U.S. Cl.
CPC .......... *A61K 9/0073* (2013.01); *A61K 31/568* (2013.01); *A61K 47/38* (2013.01)

(58) Field of Classification Search
CPC ..... A61K 9/0073; A61K 31/568; A61K 47/38
See application file for complete search history.

(56) References Cited

U.S. PATENT DOCUMENTS

| 2002/0012688 | A1 | 1/2002 | Dohi et al. | |
| 2004/0127476 | A1* | 7/2004 | Kershman | A61K 9/2095 514/177 |
| 2004/0219108 | A1* | 11/2004 | Dohi | A61K 9/0043 424/46 |
| 2005/0100564 | A1 | 5/2005 | Mattern | |
| 2007/0178166 | A1* | 8/2007 | Bernstein | A61K 9/0073 424/499 |
| 2010/0047206 | A1* | 2/2010 | Dohi | A61K 9/0043 424/85.4 |
| 2011/0033544 | A1 | 2/2011 | Nagata et al. | |
| 2012/0160944 | A1 | 6/2012 | Dodd et al. | |

FOREIGN PATENT DOCUMENTS

| EP | 0 187 433 | 7/1986 | |
| JP | 62-42888 | 9/1987 | |
| JP | 9-291025 | 11/1997 | |
| JP | 9-291026 | 11/1997 | |
| JP | 10-59841 | 3/1998 | |
| JP | 11-130659 | 5/1999 | |
| JP | 2007-1926 | 1/2007 | |
| JP | 2007-530446 | 11/2007 | |
| JP | 2012-526726 | 11/2012 | |
| JP | 2016-718 | 1/2016 | |
| WO | WO-2014144366 A1 * | 9/2014 | ............. A61K 9/006 |

OTHER PUBLICATIONS

International Search Report (ISR) dated Feb. 5, 2019 in International (PCT) Application No. PCT/JP2018/043233.
Alessia De Ascentiis et al., "Delivery of Nasal Powders of β-Cyclodextrinby Insufflation", Pharmaceutical Research, vol. 13, No. 5, pp. 734-738, ISSN: 1573-904X, 1996, cited in CA.
Written Opinion of the International Searching Authority dated Jun. 11, 2020 in International (PCT) Patent Application No. PCT/JP2018/043233.
Iwamoto, T., et al., "Reference Ranges of Serum Total and Free Testosterone in Japanese Male Adults," Journal of Japan Urology, 2004, vol. 95, No. 6, pp. 751-760, with English abstract, machine translation, cited in specification.
Extended European Search Report dated Jul. 23, 2021 in European Patent Application No. 18882058.3

* cited by examiner

*Primary Examiner* — Robert A Wax
*Assistant Examiner* — Olga V. Tcherkasskaya
(74) *Attorney, Agent, or Firm* — Wenderoth, Lind & Ponack, L.L.P.

(57) ABSTRACT

A powder preparation for nasal administration containing a particulate of steroid hormones having an average particle size of 50 to 300 μm as an active ingredient is prepared.

7 Claims, 4 Drawing Sheets

[Fig. 1]
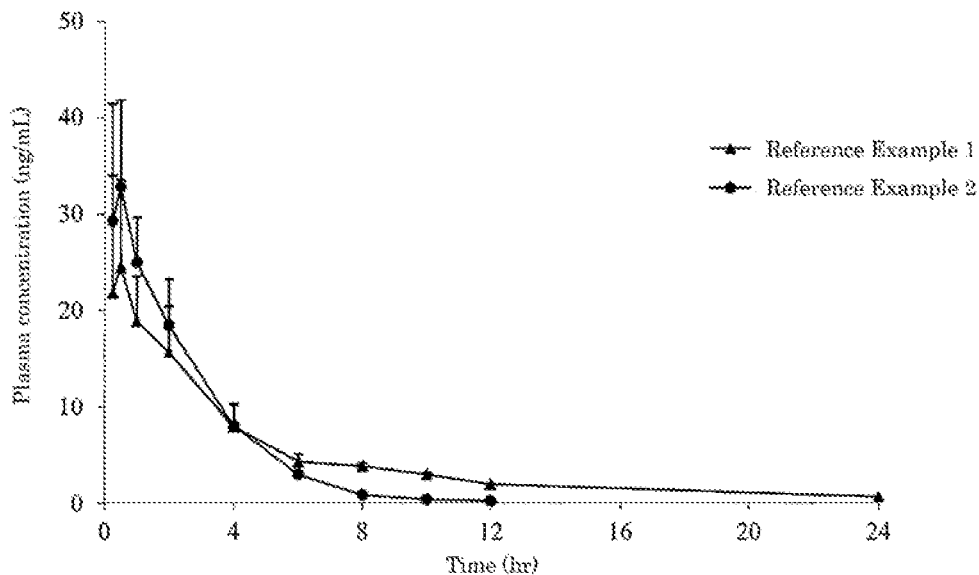
[Fig. 2]
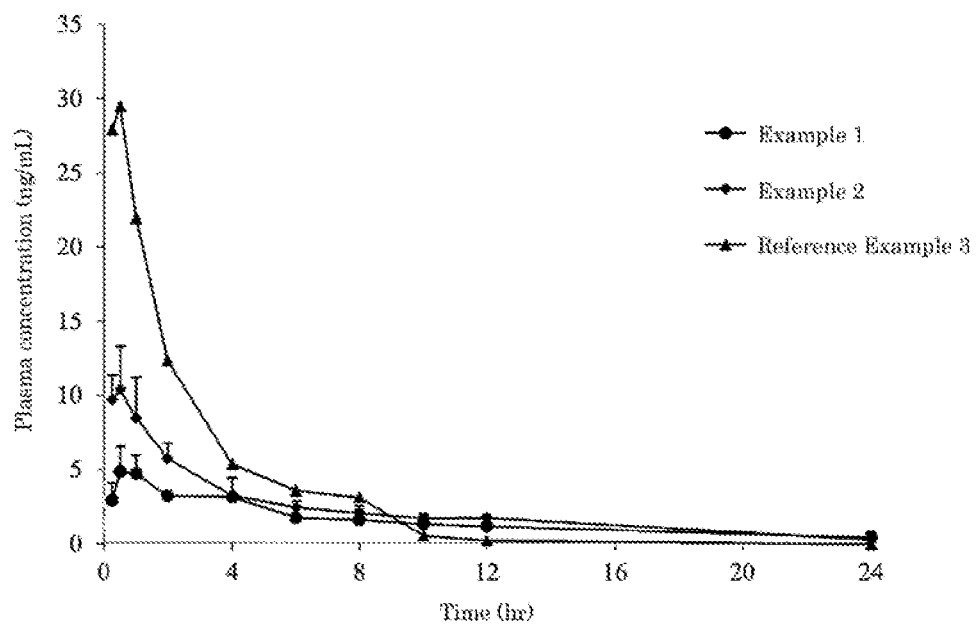

[Fig. 3]
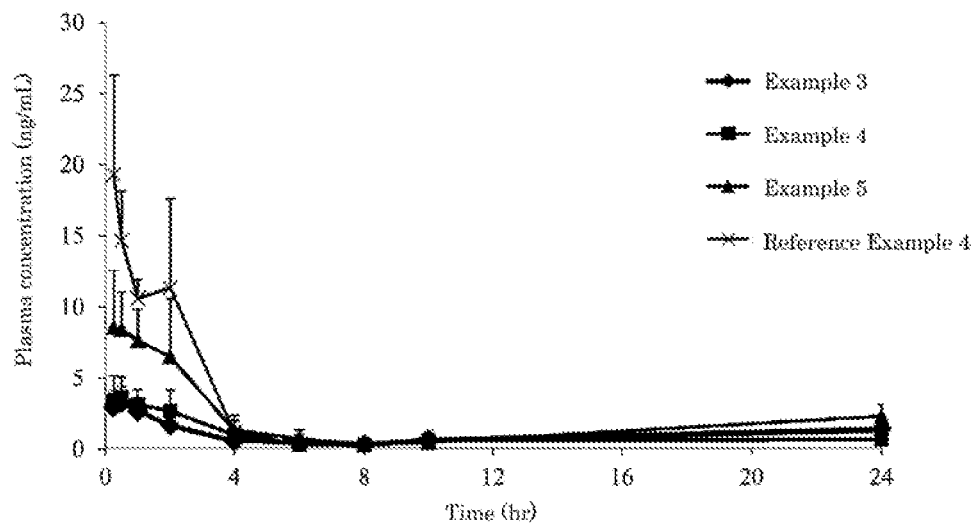
[Fig. 4]
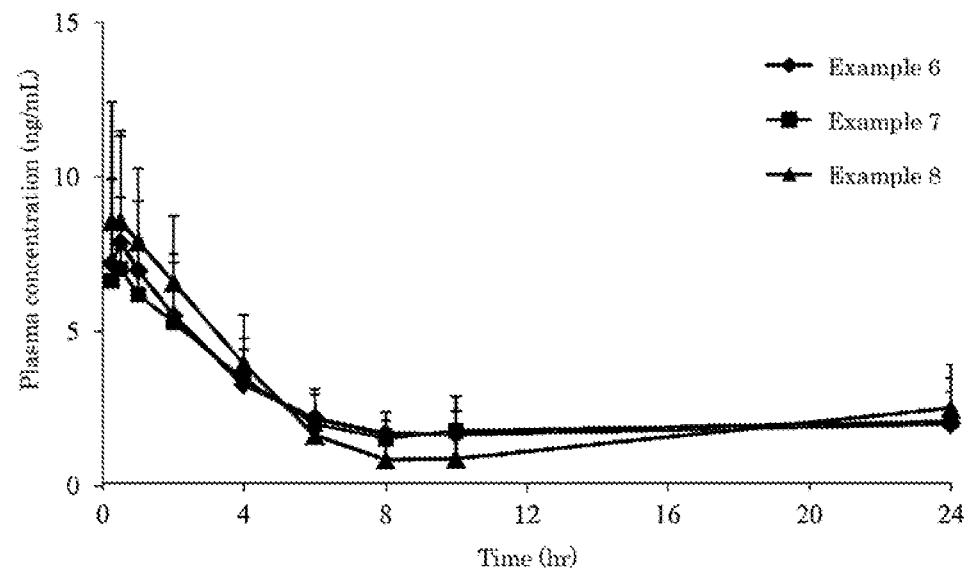

[Fig. 5]
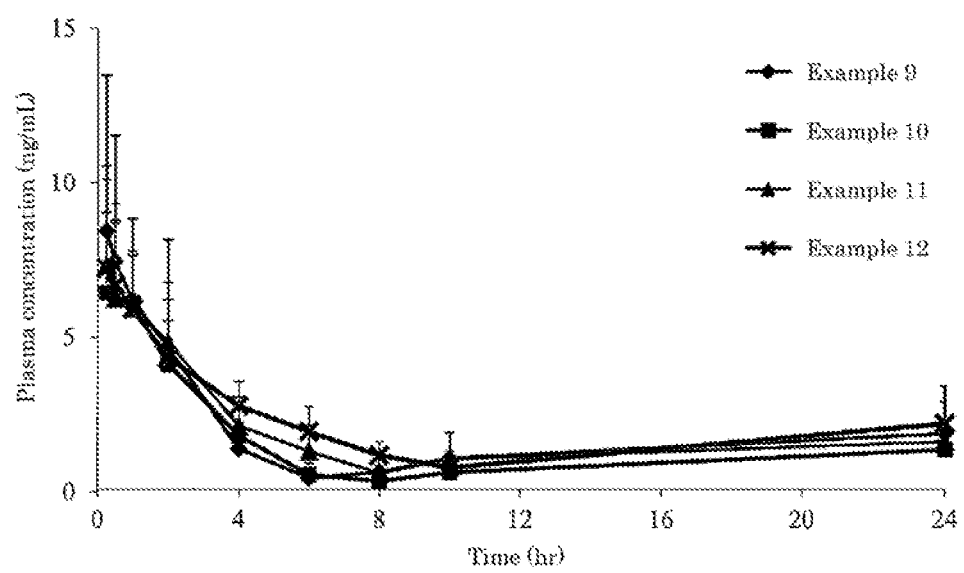
[Fig. 6]
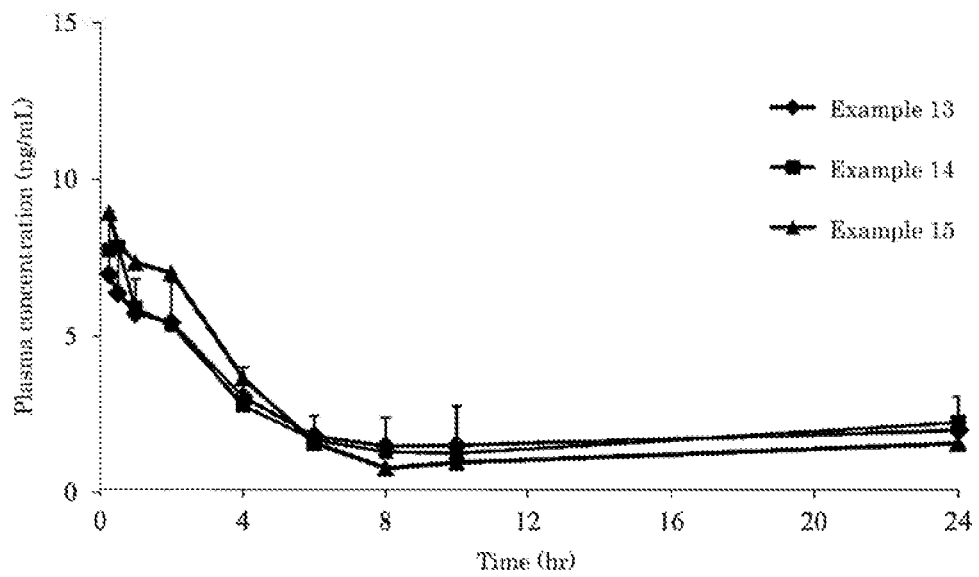

[Fig. 7]
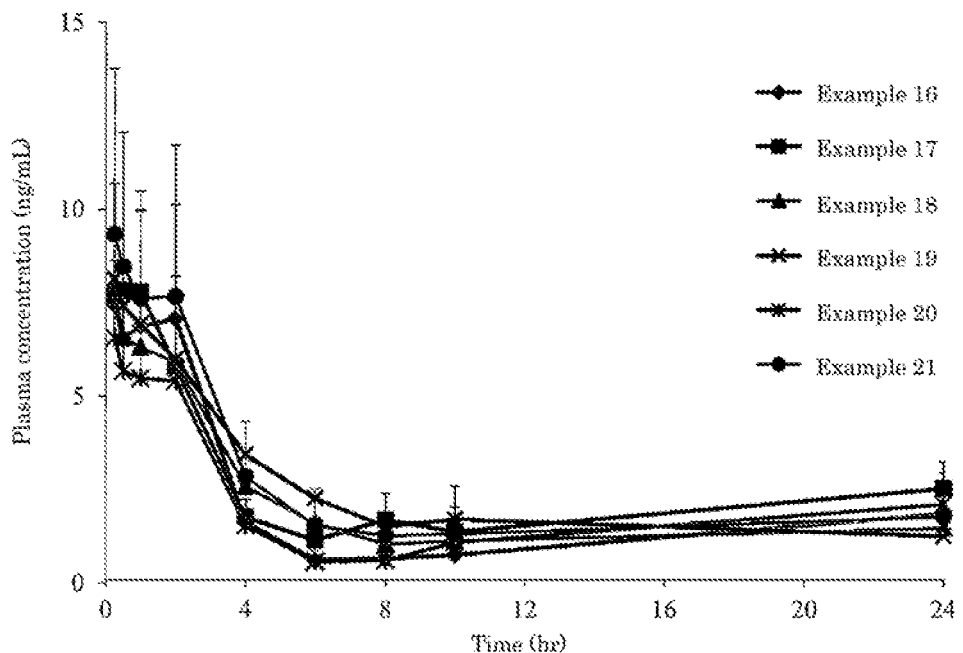
[Fig. 8]
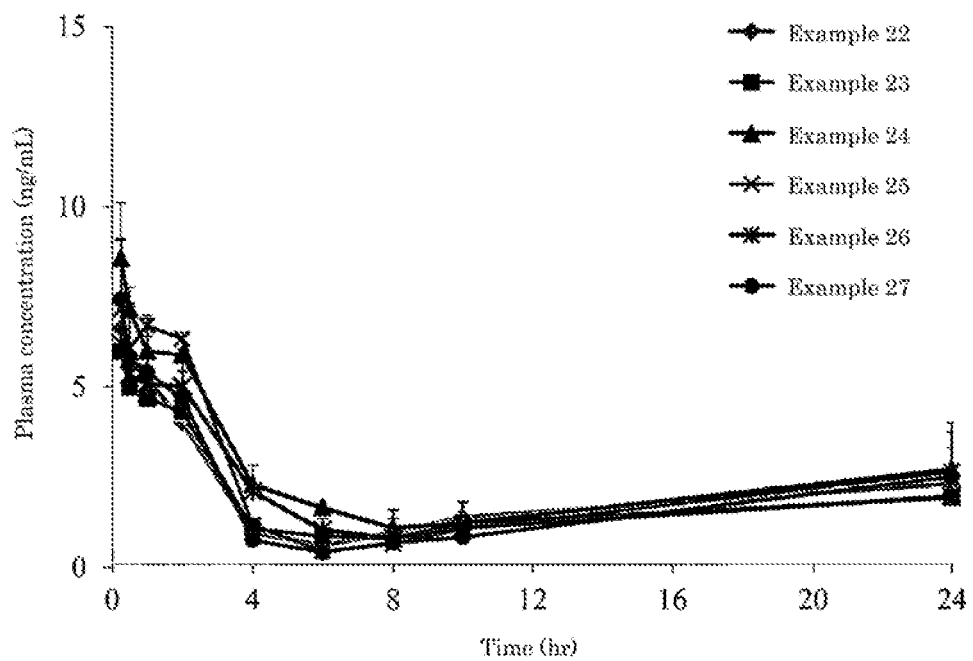

POWDER PREPARATION FOR NASAL ADMINISTRATION

TECHNICAL FIELD

The present invention relates to a powder preparation for nasal administration containing steroid hormones such as testosterone effective in treating late-onset hypogonadism (LOH syndrome).

BACKGROUND ART

Late-onset hypogonadism (LOH syndrome) has various symptoms and signs such as cognitive impairment, sleep disorder, and increased visceral fat. LOH syndrome is associated with a decrease in blood testosterone concentration, and replacement of testosterone (17β-hydroxy-3-oxo-4-androstene) can be effective.

Conventional agents for testosterone replacement therapy are mainly injections and transdermal preparations. As problems with these preparations, injections involve pain of administration site and require hospital visits for administration, and implants also have the same disadvantages. Moreover, problems of transdermal preparations are contamination of family members who have touched the applied site, dermatitis, and/or an increase in dihydrotestosterone (DHT). In either case, various side effects may occur due to a testosterone concentration rising to a non-physiological concentration immediately after administration.

Moreover, for nasal drops (liquid preparations) containing testosterone as an active ingredient, in order to take advantage of the fast-acting property that is a characteristic of transmucosal absorption, a method of reducing the particle size of testosterone to improve the in vivo absorption is attempted. Japanese Patent Application Laid-Open Publication No. H11-130659 discloses an aqueous suspended pharmaceutical composition with an improved physical stability, containing testosterone as an effective amount of a drug and about 0.05 w/w to 5% w/w crystalline cellulose and carboxymethylcellulose sodium (Avicel RC) as a suspending agent, wherein the drug particle has a spherical form with a particle size of 10 nm to 10 μm. In Examples, testosterone of 0.1 μm to 3 μm is used.

Although the liquid preparation containing testosterone with such a small particle size improves the absorption, the maximum plasma concentration ($C_{max}$) of testosterone as a criterion of testosterone replacement therapy by U.S. Food and Drug Administration (FDA) is over 15 ng/ml. For example/ the same criterion is also set for the pharmaceutical "AVEED" used for testosterone replacement therapy in the U.S. Further, the average plasma concentration ($C_{avg}$) of testosterone exceeds 2.01 to 7.5 ng/ml considered to be a plasma testosterone level (normal range) in adult male (Japanese Journal of Urology 95: 751-760, 2004), and there is concern about the occurrence of unexpected side effects. In particular, a rapid increase in blood testosterone concentration causes a subsequent rapid decrease in blood testosterone concentration, and is considered to also cause side effects such as polycythemia, elevated Prostate Specific Antigen (PSA), urinary retention, gynecomastia, and progression of sleep apnea.

Japanese Patent Application Laid-Open Publication No. 2012-526726 discloses an inhalable dry powder pharmaceutical preparation containing a therapeutic agent, wherein at least part of the therapeutic agent is present in a freebase form, and the therapeutic agent contains particles with a particle size distribution of about 5 μm to 250 μm. This document describes, as a problem to be solved by invention, the necessity to be able to engineer inhalable pharmaceutical preparations so that the pharmacokinetic profiles more closely fit clinical requirements. Specifically, this document describes, for patients with migraine, fast initial mitigation of the symptom by fast arrival of effective blood concentration or recurrence prevention by maintaining an effective blood concentration with time. In Examples, as an intranasal dry powder pharmaceutical preparation, a dry powder pharmaceutical preparation of sumatriptan or zolmitriptan that is a therapeutic agent for migraine is prepared (a free base single product with a particle size of 15 μm, a mixture product of a free base with a particle size of 15 μm and a free base having a particle size of 38 μm to 100 μm). Moreover, in Examples, although a granisetron dry powder pharmaceutical preparation is evaluated for the taste, the particle size of granisetron is not disclosed. Further, this document discloses that the dry powder pharmaceutical preparation may have no carrier or may be a mixture of a carrier and optional one or more excipients and the therapeutic agent. This document exemplifies many carriers and excipients, however, in Examples, this document does not mention a carrier and an excipient.

Japanese Patent Application Laid-Open Publication No. H09-291025 discloses a powder composition for nasal Administration comprising a drug, an absorbent and gel-forming vehicle such as a hydroxypropylcellulose, and an absorbent and poorly water-soluble vehicle such as a crystalline cellulose. This document aims to improve an absorption of a drug and to increase a maximum blood concentration of a water-soluble drug, a drug other than a hydrophobic drug, or a nonpeptide and/or nonprotein drug. Regarding the particle size of the drug, although this document discloses that it is preferred that not less than 90% by weight of the particle have a particle size of 10 μm to 350 μm, the particle size in Examples is unknown. In Examples, as the above-mentioned drug, beclometasone dipropionate being an anti-inflammatory steroid, metoclopramide being an antiemetic, leuprolide acetate being a luteinizing peptide hormone, and salmon calcitonin being a peptide hormone are used.

As described above, the conventional technology currently examines the development of the agents for testosterone replacement therapy from various viewpoints on the assumption that the particle size of testosterone is reduced as found in Japanese Patent Application Laid-Open Publication No. H11-130659. There is no attempt to control the blood testosterone concentration in the normal range by adjusting the particle size of testosterone (in particular, for a nasal powder preparation).

SUMMARY OF INVENTION

Technical Problem

It is therefore an object of the present invention to provide a powder preparation for nasal administration which can control a plasma concentration of steroid hormones such as testosterone in a specific range over a long period of time.

Another object of the present invention is to provide a powder preparation for nasal administration which inhibits a rapid increase in plasma concentration and reduces a frequency of administration and side effects.

It is still another object of the present invention to provide a powder preparation for nasal administration which can control a maximum plasma concentration ($C_{max}$) of testosterone to a plasma testosterone level for adult male and can adjust or control an average plasma testosterone concentration ($C_{avg}$) to a plasma testosterone level for adult male.

Solution to Problem

The inventors of the present invention made intensive studies to achieve the above objects and found that a plasma concentration of steroid hormones such as testosterone can be controlled in a specific range over a long period of time by adjusting or controlling an average particle size of a particulate of steroid hormones (or particulate steroid hormones) to 50 μm to 300 μm, the steroid hormones being an active ingredient of a powder preparation for nasal administration. The present invention was accomplished based on the above findings.

That is, the present invention provides a powder (or powdery) preparation for nasal administration containing a particulate of steroid hormones (or particulate steroid hormones, particle of steroid hormones, steroid hormone particle) having an average particle size of 50 μm to 300 μm as an active ingredient. The powder preparation for nasal administration may further contain a water-soluble polymer (in particular, water-soluble polysaccharides such as a cellulose having a hydroxyalkyl group). The water-soluble polymer may be free from a crystalline cellulose or a carboxymethylcellulose sodium. The water-soluble polymer may be in a particulate form. The steroid hormones may contain (or may be formed of) a male hormone (in particular, testosterone and/or a derivative thereof). The ratio of the water-soluble polymer may be about 1 part by weight to 50 parts by weight relative to 1 part by weight of the particulate of steroid hormones. The powder preparation for nasal administration may be a powder preparation for nasal administration which can control (or maintain or adjust) a maximum plasma concentration ($C_{max}$) of the steroid hormones to 15 ng/ml or less. The powder preparation for nasal administration may be a powder preparation for nasal administration which can control (or maintain or adjust) an average plasma concentration ($C_{avg}$) of the steroid hormones to 2 ng/ml to 7.5 ng/ml.

Advantageous Effects of Invention

According to the present invention, since the average particle size of the particulate of steroid hormones (or particulate steroid hormones) being an active ingredient of the powder preparation for nasal administration is adjusted to 50 μm to 300 μm, the plasma concentration of the steroid hormones such as testosterone can be controlled in the specific range over a long period of time. This allows inhibition of a rapid increase in blood concentration and reduction of a frequency of administration and side effects. For example, the side effects can also be reduced by administration twice per day. In particular, a combination testosterone as the steroid hormones and the specific water-soluble polymer can control the maximum plasma concentration ($C_{max}$) of testosterone to 15 ng/ml or less and can control the average plasma concentration ($C_{avg}$) of the steroid hormones to 2 ng/ml to 7.5 ng/ml.

BRIEF DESCRIPTION OF DRAWINGS

FIG. 1 is a graph showing a change over time of a plasma testosterone concentration in each powder preparation for nasal administration obtained in Reference Examples 1 and 2.

FIG. 2 is a graph showing a change over time of a plasma testosterone concentration in each powder preparation for nasal administration obtained in Examples 1 to 2 and Reference Example 3.

FIG. 3 is a graph showing a change over time of a plasma testosterone concentration in each powder preparation for nasal administration obtained in Examples 3 to 5 and Reference Example 4.

FIG. 4 is a graph showing a change over time of a plasma testosterone concentration in each powder preparation for nasal administration obtained in Examples 6 to 8.

FIG. 5 is a graph showing a change over time of a plasma testosterone concentration in each powder preparation for nasal administration obtained in Examples 9 to 12.

FIG. 6 is a graph showing a change over time of a plasma testosterone concentration in each powder preparation for nasal administration obtained in Examples 13 to 15.

FIG. 7 is a graph showing a change over time of a plasma testosterone concentration in each powder preparation for nasal administration obtained in Examples 16 to 21.

FIG. 8 is a graph showing a change over time of a plasma testosterone concentration in each powder preparation for nasal administration obtained in Examples 22 to 27.

DESCRIPTION OF EMBODIMENTS

Active Ingredient

The powder (or powdery) preparation for nasal administration of the present invention contains a particulate of steroid hormones (particulate steroid hormones, steroid hormone particulates, steroid hormone particles) having an average particle size of 50 μm to 300 μm as an active ingredient (a pharmacologically or biologically active ingredient). The steroid hormones are classified roughly into male hormones (androgen), female hormones (estrogen), and corticoids. The male hormone may include, for example, testosterone, a testosterone derivative [for example, a $C_{1-4}$alkyltestosterone such as methyltestosterone; a $C_{1-18}$alkanoic acid ester of testosterone such as testosterone acetate, testosterone propionate, testosterone isocaproate, testosterone enanthate, testosterone decanoate, or testosterone undecanoate; a cycloalkanoic acid ester of testosterone such as testosterone butylhexanoate (Testosterone buciclate); dihydrotestosterone (DHT); and dehydroepiandrosterone (DHEA)], and drostanolone. Examples of the female hormones may include an estrogen such as estradiol, estriol, estrone, or fosfestrol, and a gestagen such as progesterone, norethisterone, or pregnanediol. The corticoids may include, for example, dexamethasone phosphate, fludrocortisone acetate, methylprednisolone sodium succinate, and hydrocortisone phosphate. These steroid hormones may be used alone or in combination.

Among them, a steroid hormone (in particular, a male hormone) is preferred, and testosterone or a derivative thereof (in particular, testosterone) is particularly preferred.

The form (or shape) of the particulate of steroid hormones is any particulate (or powdery) form without limitation to a specific one, and may be an isotropic form (such as a spherical or substantially spherical form or a cubic form) or may be an anisotropic form (such as an ellipsoidal form, a polyhedral form, a rectangular parallelepiped form, a fiber form, or an amorphous form).

According to the present invention, since the particulate of steroid hormones has a specific average particle size and has a particle size adjusted in a specific range, the plasma concentration of the steroid hormones can be controlled in a specific range for a long period of time. The volume average particle size (D50) of the steroid hormones is 50 μm to 300 μm and may be preferably about 70 μm to 250 μm and more preferably about 100 μm to 230 μm (for example, about 150 μm to 200 μm). From the viewpoint of inhibiting a rapid increase in plasma concentration and reducing a frequency of administration and side effects, the volume average particle size may be, for example, about 50 μm to 200 μm, preferably about 80 μm to 150 μm, and more preferably about 90 μm to 130 μm (particularly about 100 μm to 120 μm). In a case where the average particle size is excessively large, the powder preparation for nasal administration provides a low maximum plasma concentration ($C_{max}$) of the steroid hormones. In a case where the average particle size is excessively small, the powder preparation for nasal administration provides a low average plasma concentration ($C_{avg}$) of the steroid hormones. Herein and in the claims, in a case where the form of the particulate of steroid hormones is an anisotropic form, the particle sire of each particle means an average value of a major axis and a minor axis.

It is preferred that the steroid hormones preferably have a narrower particle size distribution (particle size distribution). The particle size (D90) at a cumulative frequency of 90% is about 100 μm to 300 μm, preferably about 120 μm to 280 μm, and more preferably about 150 μm to 250 μm (particularly about 200 μm to 240 μm).

A method of preparing steroid hormones having a narrow particle size distribution (a method of controlling a particle size) may use a conventional powder processing apparatus. For example, uniform particles may be prepared using a commercially available surface modification processing apparatus ("NOBILTA NOB-MINI" manufactured by HOSOKAWA MICRON CORPORATION).

Herein and in the claims, the volume average particle size and the particle size distribution of the particulate of steroid hormones can be measured using a laser diffraction particle size analyzer, specifically, can be measured according to the method described in Examples mentioned below.

The active ingredient may contain other active ingredients in addition to the particulate of steroid hormones. Other active ingredients are any active ingredient having a pharmacological action and may include, but should not be limited to, for example, other hormones such as pancreatic circulatory hormones, prostaglandins, steroids, corticoids, thyroid hormones, and growth hormones.

The proportion of the particulate of steroid hormones in the active ingredient may be, for example, not less than 50% by weight, may be preferably not less than 80% by weight, more preferably not less than 90% by weight, or may be 100% by weight (the active ingredient contains only the particulate of steroid hormones).

Water-Soluble Polymer

The powder preparation for nasal administration of the present invention further contains a water-soluble polymer in addition to the active ingredient. According to the present invention, a combination of the active ingredient having the above-mentioned particle size and the water-soluble polymer allows further effective control (or adjustment) of the plasma concentration of the steroid hormones.

The water-soluble polymer may include a water-soluble synthetic polymer, water-soluble polysaccharides, or others. The water-soluble synthetic polymer may be used alone, the water-soluble polysaccharides may be used alone, or the water-soluble synthetic polymer and the water-soluble polysaccharides may be used in combination.

The water-soluble synthetic polymer may include, for example, a copolyvidone such as a polyvinylpyrrolidone (PVP) or a copolymer of vinylpyrrolidone and vinyl acetate sold under the trademark KOLLIDON, a polyvinyl alcohol (PVA), a carboxyvinyl polymer, a polyacrylic polymer, and a polyethylene glycol. These water-soluble synthetic polymers may be used alone or in combination.

The water-soluble polysaccharides are pharmacologically or physiologically acceptable polysaccharides. Examples of the polysaccharides may include a soluble starch such as a pregelatinized starch, a partially pregelatinized starch, or a sodium carboxymethylstarch; cellulose ethers such as a methylcellulose (MC), a carboxymethylcellulose (carmellose or CMC), a carboxymethylcellulose sodium (CMC-Na), a carboxymethylcellulose calcium, a hydroxyethylcellulose (HEC), a hydroxypropylcellulose (HPC), and a hydroxypropylmethylcellulose (HPMC); cellulose esters such as a cellulose phthalate and a hydroxypropylmethylcellulose phthalate; homopolysaccharides such as a chitin, a chitosan, and a pullulan; and heteropolysaccharides such as a gum arabic (gum acacia), a xanthan gum, a locust bean gum, a tragacanth gum, and a sodium alginate. These water-soluble polysaccharides may be used alone or in combination.

Among these water-soluble polymers, a water-soluble polymer which forms a gel with water and easily adheres to the nasal mucosa is preferred. For example, the above-exemplified water-soluble synthetic polymer and water-soluble polysaccharides are preferred. Specifically, the water-soluble polysaccharides (such as MC, CMC, CMC-Na, HEC, HPC, and HPMC) are preferred, and a cellulose having a hydroxyalkyl group (in particular, hydroxypropyl group) (e.g., a hydroxy$C_{2-4}$alkylcellulose such as HEC or HPC, and a hydroxy$C_{2-4}$alkyl$C_{1-4}$alkylcellulose such as HPMC) is particularly preferred. Among them, a combination of a hydroxyalkylcellulose (in particular, a hydroxy$C_{2-3}$alkylcellulose such as a hydroxypropylcellulose) and the particulate of steroid hormones having the above-mentioned particle size (in particular, testosterone) allows effective control (or adjustment) of the average plasma concentration ($C_{avg}$), and thus inhibition of an excessive increase in the maximum plasma concentration ($C_{max}$) and control (or adjustment) of the average plasma concentration ($C_{avg}$) are compatible.

The proportion of the cellulose having a hydroxyalkyl group (for example, a cellulose having hydroxypropyl group, such as a hydroxypropylcellulose or a hydroxypropylmethylcellulose) in the water-soluble polysaccharides may be, for example, not less than 50% by weight, may be preferably not less than 80% by weight and more preferably not less than 90% by weight, or may be 100% by weight (the water-soluble polysaccharides contain only the cellulose having a hydroxyalkyl group). According to the present invention, the polysaccharides may be free from a crystalline cellulose.

The water-soluble polymer (in particular, the water-soluble polysaccharides such as a hydroxypropylcellulose), e.g., for 2% by weight aqueous solution at 20° C. may have a viscosity of, for example, about 2 mPa·s to 10000 mPa·s, preferably about 10 mPa·s to 8000 mPa·s (e.g., about 100 mPa·s to 7000 mPa·s), and more preferably about 120 mPa·s to 5000 mPa·s (particularly about 150 mPa·s to 4000 mPa·s). The above-mentioned viscosity may be selected depending on the application, may be about 50 mPa·s to 1000 mPa·s (particularly about 100 mPa·s to 500 mPa·s). In a case where the handleability is concerned, for example, the viscosity may be about 500 mPa·s to 5000 mPa·s (particularly about 1000 mPa·s to 4000 mPa·s). A water-soluble polymer having an excessive low viscosity may have a low handleability. Herein and in the claims, the viscosity can be measured by a capillary viscometer method or a rotational viscometer method.

The number-average molecular weight (Mn) of the water-soluble polymer (in particular, the water-soluble polysaccharides such as a hydroxypropylcellulose) nay be, for example, about 100,000 to 5,000,000, preferably about 300,000 to 2,000,000, and more preferably about 500,000 to 1,500,000 in terms of a polystyrene using GPC (gel permeation chromatography). The molecular weight may be selected depending on the application, for example, may be about 500,000 to 1,000,000 (particularly about 600,000 to 800,000). In a case where the handleability us concerned, for example, the molecular weight may be about 700,000 to 1,500,000 (particularly about 800,000 to 1,000,000).

The form (or shape) of the water-soluble polymer is not particularly limited to a specific one. For example, the form of the water-soluble polymer may be a particulate form that is independent of the particulate of steroid hormones, may be a composite form with the steroid hormones (e.g., a form covering or adhering to the surface of the steroid hormones), or may be a combination of the particulate form and the composite form. Among them, the particulate form is preferred.

The form (or shape) of the particulate water-soluble polymer (or the particulate of water-soluble polymer) is not particularly limited to a specific one and may be an isotropic form (such as a spherical or substantially spherical form, or a cubic form) or may be an anisotropic form (such as an ellipsoidal form, a polyhedral form, a rectangular parallelepiped form, a fiber form, or an amorphous form). Among them, the isotropic form or a form near the isotropic form is preferred. The ratio of the major axis relative to the minor axis may be, for example, not more than 100 or may be preferably not more than 10 and more preferably not more than 5 (particularly not more than 3).

The particulate water-soluble polymer (in particular, the water-soluble polysaccharides such as a hydroxypropylcellulose; may have a volume average particle size (D50) of, for example, about 10 µm to 500 µm, preferably about 30 µm to 300 µm, and more preferably about 40 µm to 200 µm (particularly about 50 µm to 150 µm). Moreover, the average particle size of the particulate water-soluble polymer may be, for example, about 0.1 times to 10 times, preferably about 0.2 times to 5 times (e.g., about 0.3 times to 1 time), and more preferably about 0.4 times to 0.8 times (particularly about 0.5 times to 0.7 times) as large as the average particle size of the particulate of steroid hormones. A particulate water-soluble polymer having an excessively large average particle size may have difficulty in uniformly nixing with the particulate of hormones. A particulate water-soluble polymer having an excessively small average particle size may also have difficulty in uniformly mixing with the particulate of hormones. The volume average particle size of the particulate water-soluble polymer can be measured by the same method as that for the average particle size of the particulate of steroid hormones.

The ratio of the water-soluble polymer relative to 1 part by weight of the particulate of steroid hormones is, for example, about 1 parts by weight to 50 parts by weight, preferably about 3 parts by weight to 30 parts by weight, and more preferably about 4 parts by weight to 20 parts by weight (particularly about 4 parts by weight to 15 parts by weight). In a case where the ratio of the water-soluble polymer is excessively low, it may be impossible to effectively control (or adjust) the average plasma concentration ($C_{avg}$).

Other Ingredients

The powder preparation for nasal administration of the present invention may further contain an excipient in addition to the active ingredient arid the water-soluble polymer. The excipient may include, for example, saccharides or sugar alcohols such as lactose, white sugar or refined sugar, glucose, sucrose, mannitol, sorbitol, and xylitol; and a microcrystalline cellulose. These excipients may be used alone or in combination. The ratio of the excipient relative to 100 parts by weight of the particulate of steroid hormones is, for example, about 0.1 parts by weight to 100 parts by weight, preferably about 1 parts by weight to 50 parts by weight, and more preferably about 3 parts by weight to 30 parts by weight.

The powder preparation for nasal administration of the present invention may further contain other ingredients if necessary. Other ingredients are pharmacologically or physiologically acceptable ingredients. Examples of other ingredients may include a binder (for example, starches such as a corn starch and a dextrin; celluloses such as a crystalline cellulose (also including a microcrystalline cellulose) and an ethylcellulose (EC); and a synthetic polymer such as a polylactic acid), a disintegrant (for example, calcium carbonate, a croscarmellose sodium, and a crosslinked polyvinylpyrrolidone), a lubricant, a disintegrant aid, an antioxidant or an oxidation inhibitor, a stabilizer, an antiseptic agent or a preservative, a fungicide or an antibacterial agent, an antistatic agent, a corrigent or a masking agent, a coloring agent, a deodorant or a perfume, an algefacient, and an antifoaming agent. These other ingredients may be used alone or in combination. The ratio of other ingredients relative to 100 parts by weight of the particulate of steroid hormones is, for example, about 0.1 parts by weight to 100 parts by weight, preferably about 1 parts by weight to 50 parts by weight, and more preferably about 3 parts by weight to 30 parts by weight.

Characteristics of Powder Preparation for Nasal Administration

The powder preparation for nasal administration of the present invention is in a powder (particulate) form containing the above-mentioned particulate of steroid hormones. In a case where the water-soluble polymer is combined with the particulate of steroid hormones, the preparation may be a composite particle in which the water-soluble polymer is compound with the particulate of steroid hormones, may be a mixture of the particulate of steroid hormones and the particulate water-soluble polymer, or may be a mixture of the composite particle, the particulate of steroid hormones, and the particulate water-soluble polymer.

As a method of producing the composite particle, there may be used a conventional granulation method. The granulation method may be either a dry granulation method (for example, a dry shredding granulation method and a compression molding granulation method) or a wet granulation method (for example, an extruding granulation method a tumbling granulation method, a fluidized bed granulation method, a mixing agitation granulation method, a spray drying granulation method, and a vibration granulation method). Among them, the wet granulation method or other methods are widely used. The obtained granule may be pulverized and/or sized if necessary. The composite particle may have a volume average particle size (D50) of, for example, about 100 μm to 500 μm, preferably about 120 μm to 300 μm, and more preferably about 150 μm to 250 μm. The volume average particle size of the composite particle can be measured by the same method as that for the average particle size of the particulate of steroid hormones.

The method of producing the particulate of steroid hormones and that of producing the particulate water-soluble polymer may be any of the above-mentioned dry granulation method and the above-mentioned wet granulation method. Among the granulation methods, the dry shredding granulation method is widely used in terms of simplicity or others. For the pulverization, there may be usually employed a pulverizer used for pulverization of pharmaceuticals, for example, an atomizer (such as a sample mill or a hammer mill), a pin mill, a jet mill, and a ball mill.

As the method of mixing the mixture, there may be used a conventional method, for example, a method using a rotary vessel mixer such as a V-shaped mixer or a container mixer, a fixed vessel mixer such as a ribbon mixer or a high-speed mixer, or other mixers. The powder preparation for nasal administration of the present invention is preferably a mixture of the particulate of steroid hormones and the particulate water-soluble polymer. In this mixture, it is preferred that the particulate of steroid hormones and the particulate water-soluble polymer be mixed uniformly.

The powder preparation for nasal administration of the present invention can inhibit an excessive increase in the maximum plasma concentration ($C_{max}$) of the steroid hormones (in particular, testosterone. The maximum plasma concentration ($C_{max}$) may be, for example, not more than 25 ng/ml, preferably not more than 18 ng/ml, and more preferably not more than 15 ng/ml (particularly not more than 7.5 ng/ml).

The powder preparation for nasal administration of the present invention can also control (or reduce) the change (the average plasma concentration ($C_{avg}$)) of the plasma concentration of the steroid hormones (in particular, testosterone). For example, the powder preparation can maintain the average plasma concentration ($C_{avg}$) within the range from 1 ng/ml to 10 ng/ml, preferably 2 ng/ml to 7.5 ng/ml, and more preferably 2.5 ng/ml to 7 ng/ml. Further, the control of the change can be maintained over 12 hours.

Since the powder preparation for nasal administration of the present invention has a small change of the blood concentration of the steroid hormones, the steroid hormones (in particular, testosterone) have a late time ($T_{max}$) to reach the maximum plasma concentration ($C_{max}$). For example, the $T_{max}$ may be not less than 0.1 hours (e.g., 0.1 hour to 3 hours), preferably not less than 0.3 hours, and more preferably not less than 0.5 hours (particularly not less than 0.8 hours).

Since the powder preparation for nasal administration of the present invention of the present invention has a small change of the plasma concentration of the steroid hormones, the steroid hormones (in particular, testosterone) also have a long elimination half-life ($t_{1/2}$), where the elimination half-life ($t_{1/2}$) is the time required for the plasma concentration to reach half, of the maximum plasma concentration ($C_{max}$). For example, the $t_{1/2}$ may be not less than 2 hours (e.g., 2 hours to 10 hours), preferably not less than 3 hours, and more preferably not less than 5 hours (particularly not less than 6 hours).

The powder preparation for nasal administration of the present invention also allows the control (or adjustment) of the average plasma concentration ($C_{avg}$) of the steroid hormones (in particular, testosterone). For example, the powder preparation can control (or adjust) the average plasma concentration ($C_{avg}$) to 3 ng/ml to 10 ng/ml that is the endpoint of testosterone replacement therapy clinical trial shown by FDA.

The powder preparation for nasal administration of the present invention has a long mean residence time in plasma $MRT_{0-\infty}$). For example, the mean residence time in plasma ($MRT_{0-\infty}$) may be not less than 3 hours (e.g., about 3 hours to 20 hours) or may be, for example, not less than 4 hours, preferably not less than 5 hours, and more preferably net less than 6 hours (particularly not less than 7 hours).

Herein and in the claims, the maximum plasma concentration ($C_{max}$), the time to reach the maximum plasma concentration ($T_{max}$), the elimination half-life ($t_{1/2}$), the average plasma concentration ($C_{avg}$), and the mean residence time in plasma ($MRT_{0-\infty}$) can be evaluated according to the methods described in the after-mentioned Examples.

Since the powder preparation for nasal administration of the present invention inhibits an excessive increase in the maximum plasma concentration ($C_{max}$) and has less side effects, the powder preparation also has an excellent safety. Thus, the powder preparation can safely be administered to human beings and non-human animals, usually, mammals (for example, human beings, rabbits, dogs, cats, bovines, horses, pigs, and monkeys).

The powder preparation for nasal administration of the present invention is in any powdery form that may be powders, fine granules, granules, sprays, and aerosols. The method of administration is any administration to the nasal cavities such as spraying and may be selected depending to the species of the preparation without specific limitation.

The frequency of administration is not particularly limited to a specific one. For example, the frequency of administration may be once per day or may be a plurality of times per day (e.g., twice to three times per day) if necessary. Since the excessive increase in the maximum plasma concentration ($C_{max}$) is inhibited and the plasma testosterone concentration is stabilized over 12 hours, the frequency of administration may be twice per day.

The amount to be administered (or dose) may be selected according to the species, age, body weight, and condition (e.g., a performance status, a condition of a disease, a presence of a complication) of the subject to be administered, the duration (or period or schedule) of administration, the dosage form, the method (or route) of administration, and others. For example, the amount to be administered (or dose) to human beings (daily dose) is about 0.01 mg/day to 50 mg/day, preferably about 0.05 mg/day to 30 mg/day (e.g., about 0.1 mg/day to 20 mg/day), more preferably about 0.5 mg/day to 15 mg/day (particularly about 1 mg/day to 10 mg/day).

EXAMPLES

The following examples are intended to describe this invention in further detail and should by no means be interpreted as defining the scope of the invention. Incidentally, the details of raw materials used and the method of measuring an average particle size are as follows.

Raw Materials

Testosterone A: testosterone manufactured by Tokyo Chemical Industry Co., Ltd., volume average particle size (D50) 123 μm Testosterone B: testosterone manufactured by SIGMA-ALDRICH, volume average particle size (D50) 184 μm Testosterone C: testosterone manufactured by Bayer, volume average particle size (D50) 273 μm Hydroxypropylcellulose H: "HPC-H" manufactured by Nippon Soda Co., Ltd., volume average particle size (D50) 80 to 110 μm, viscosity (2% by weight aqueous solution, 20° C.) 1000 mPa·s to 4000 mPa·s, molecular weight (GPC method) 910,000

Hydroxypropylcellulose M: "HPC-M" manufactured by Nippon Soda Co., Ltd., viscosity (2% by weight aqueous solution, 20° C.) 150 mPa·s to 400 mPa·s, molecular weight (GPC method) 700,000

Hydroxypropylcellulose L: "HPC-L" manufactured by Nippon Soda Co., Ltd., viscosity (2% by weight aqueous solution, 20° C.) 6 mPa·s to 10 mPa·s, molecular weight (GPC method) 140,000

Crystalline cellulose: "CEOLUS PH-F20JP" manufactured by Asahi Kasei Chemicals Corp.

Pregelatinized starch: "MX-1" manufactured by Asahi Kasei Chemicals Corp., viscosity (2% by weight aqueous solution, 25° C.) 70 mPa·s Carboxyvinyl polymer: "974P" manufactured by Lubrizol Corporation, viscosity (2% by weight, pH 7.5) 294,000 mPa·s to 394,000 mPa·s, molecular weight 500,000 to 5,000,000

Sodium alginate: "I-8" manufactured by KIMICA Corporation, viscosity (1% by weight aqueous solution, 20° C.) 800 mPa·s to 900 mPa·s, molecular weight 1,000,000 to 4,000,000

Hydroxypropylmethylcellulose: "90SH-15000SR" manufactured by Shin-Etsu Chemical. Co., Ltd., viscosity (2% by weight aqueous solution, 20° C.) 15,000 mPa·s, molecular weight 10,000 to 200,000

Polyvinylpyrrolidone: "K-90" manufactured by BASF, viscosity (10 w/v % aqueous solution, 20° C.) 300 mPa·s to 700 mPa·s, molecular weight 360,000

Xanthan gum: "CG-F" manufactured by Sansho Co., Ltd., viscosity (1% by weight aqueous solution, addition of 1% by weight KCl) 1200 mPa·s to 1600 mPa·s, molecular weight 2,000,000 to 50,000,000

Polyethylene glycol: "6000" manufactured by Sanyo Chemical Industries, Ltd., viscosity (500 g/L aqueous solution, 25° C.) 200 mPa·s to 400 mPa·s, molecular weight 7300 to 9300

Polyvinyl alcohol: "EG-18" manufactured by The Nippon Synthetic Chemical Industry Co., Ltd., viscosity (4% by weight aqueous solution) 18.3 mPa·s, molecular weight 30,000 to 110,000

Chitosan: "F" manufactured by KIMICA Corporation, viscosity (0.5% by weight aqueous solution, 20° C.) 5 mPa·s to 20 mPa·s, molecular weight 10,000 to 1,000,000

Carmellose sodium: "PR-S" manufactured by DKS Co. Ltd., viscosity (2% by weight aqueous solution, 25° C.) 20 mPa·s to 40 mPa·s, molecular weight 6,000 to 30,000

Locust bean gum: "RL-200Z" manufactured by KIMICA Corporation, viscosity (aqueous solution dissolved at 85° C.) 3000 mPa·s to 4000 mPa·s, molecular weight 300,000

Copolyvidone: "VA64" manufactured by BASF, viscosity (5% by weight aqueous solution, 25° C.) 5 mPa·s, molecular weight 50,000

Lactose: lactose hydrate, manufactured by DFE Pharma

Method of Measuring Particle Size

A particle size was measured by a dry dispersion method (unit) using a laser diffraction particle size analyzer ("MASTERSIZER 3000" manufactured by Malvern).

Reference Examples 1 and 2

(1) Formulation of Preparation

The formulations of preparations of Reference Examples 1 and 2 are shown in Table 1 below.

TABLE 1

| Ingredient | Reference Example 1 | Reference Example 2 |
| --- | --- | --- |
| Testosterone A | 5 mg | 5 mg |
| Hydroxypropylcellulose H | 5 mg | — |
| Crystalline cellulose | — | 5 mg |

(2) Formulation Process

Testosterone A was pulverized in a mortar, and then Hydroxypropylcellulose K or Crystalline cellulose was added and mixed thereto. The mixture was filled into a cylindrical device to give a preparation for administration.

Incidentally, the cylindrical device is a device that is a needle protector (made of plastic) for a spinal needle ("Terumo Spinal Needle (registered trademark)" manufactured by Terumo Corporation), the protector having a tip smoothed with a file. In all examples, this container was connected to an oxygen gas spray can (gas for laboratory) to spray a preparation.

(3) Pharmacokinetic Evaluation

For each one of aged female dogs (three dogs), a cylindrical device filled with the preparation was inserted 1 cm into one of the nasal cavities, and a single nasal dose was administered (the amount of testosterone administered: 5 mg). At 0.25, 0.5, 1, 2, 4, 6, 9, 10, 12, and 24 hours after the nasal administration, the blood was collected using a 23G needle and a heparin-treated syringe. The blood collection volume was about 1 ml per point of time. The collected blood was centrifuged (15000 rpm, 2 minutes, 4° C.), and then the plasma was collected and was cryopreserved in a freezer (−20° C. or less) until the time of measurement. The plasma testosterone concentration was measured under the following analysis conditions.

HPLC Condition

HPLC: Prominence series (manufactured by SHIMADZU CORPORATION)
Column: Scherzo SM-C18 (2.0 mmi.d.×50 mm, 3 μm, manufactured by Imtakt Corporation)
Mobile phase A: 0.1 vol % acetic acid aqueous solution
Mobile phase B: acetonitrile
Column temperature: 40° C.
Temperature in autosampler: room temperature
Flow rate: 0.3 ml/min
Injection volume: 10 μL
Gradient condition: shown in the following Table 2

TABLE 2

| Time (min) | 0 | 4 | 5 | 5.1 | 7.5 |
|---|---|---|---|---|---|
| Mobile phase A (%) | 70 | 35 | 0 | 70 | 70 |
| Mobile phase B (%) | 30 | 65 | 100 | 30 | 30 |

MS Condition

MS/MS: 3200QTRAP (manufactured by AB Sciex)
Ionization method: ESI method (Electrospray Ionization)
Ion polarity: Positive
Measurement ion: shown in the following Table 3

TABLE 3

| Measuring object | Precursor ion $[M + H]^+$ (m/z) | Product ion (m/z) | DP (V) | CE (eV) |
|---|---|---|---|---|
| Testosterone A | 289.1 | 109.1 | 51 | 33 |
| Testosterone-$d_3$ | 292.0 | 109.1 | 56 | 35 |

The obtained plasma testosterone concentration was analyzed by a pharmacokinetic analysis software (Phoenix WinNonlin Version 6.4: manufactured by Certara GK) to calculate a maximum plasma concentration ($C_{max}$), an area under the plasma concentration-time curve to the time of the last quantifiable measurement (or an area under the plasma concentration-time curve to the time of the last measurement at which the measurement value was not less than the quantitative lower limit) ($AUC_{0-t}$), an area under the plasma concentration-time curve extrapolated to infinity ($AUC_{0-\infty}$), a time to reach a maximum plasma concentration ($T_{max}$), an elimination half-life ($t_{1/2}$), and a mean residence time in blood ($MRT_{0-\infty}$).

Table 4 shows the pharmacokinetic parameters of the obtained preparations. The plasma testosterone concentration profile is shown in FIG. 1.

TABLE 4

| | $T_{max}$ (hr) | $C_{max}$ (ng/ml) | $AUC_{0-t}$ (ng·hr/ml) | $AUC_{0-\infty}$ (ng·hr/ml) | $t_{1/2}$ (hr) | $MRT_{0-\infty}$ (hr) |
|---|---|---|---|---|---|---|
| Reference Example 1 | 0.4 | 25.7 | 109.3 | 125.4 | 9.40 | 9.70 |
| Reference Example 2 | 0.4 | 34.4 | 90.9 | 92.1 | 2.67 | 2.47 |

As apparent from the results shown in Table 4 and FIG. 1, the preparation containing the hydroxypropylcellulose as saccharides lowers the maximum plasma concentration ($C_{max}$) and prolongs the elimination half-life ($t_{1/2}$) and the mean residence time in plasma ($MRT_{0-\infty}$) compared with the preparation containing the crystalline cellulose, thus maintaining the plasma testosterone concentration for a longer period of time.

Examples 1 to 2 and Reference Example 3

(1) Formulation of Preparation

The formulations of preparations of Examples 1 to 2 and Reference Example 3 are shown in Table 5 below.

TABLE 5

| Ingredient (average particle size) | Example 1 | Example 2 | Reference Example 3 |
|---|---|---|---|
| Testosterone B classified product (184 μm) | 2 mg | — | — |
| Testosterone B classified product (90.4 μm) | — | 2 mg | — |
| Testosterone B pulverized product (16.2 μm) | — | — | 2 mg |
| Hydroxypropylcellulose H | 18 mg | 18 mg | 18 mg |

(2) Formulation Process

To a classified product of Testosterone B or a pulverized product thereof [a classified product which was classified by sieving Testosterone B and of which the volume average particle size was measured after classification (a volume average particle size of 184 μm: Example 1, 90.4 μm: Example 2), and a pulverized product which was obtained by pulverizing Testosterone B in a mortar and of which the volume average particle size was measured after pulverization (a volume average particle size of 16.2 μm: Reference Example 3)] was added and mixed Hydroxypropylcellulose H. The mixture was filled into a cylindrical device to give a preparation for administration.

(3) Pharmacokinetic Evaluation

For each one of aged female dogs (three dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, 12, and 24 hours after the nasal administration, the blood was collected using a 23G needle and a syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: Nexora X2 (manufactured by SHIMADZU CORPORATION)
Column: Kinetex 2.6 μm EVO C18 (4.6 mmi.d.×150 mm, 2.6 μm, manufactured by Phenomenax)
Mobile phase A: 0.05 vol % acetic acid aqueous solution
Mobile phase B: methanol
Column temperature: 45° C.
Temperature in sample chamber: 10° C.
Injection volume: 10 μL
Gradient condition: shown in the following Table 6

TABLE 6

| Time (min) | Mobile phase A (%) | Mobile phase B (%) | Flow rate (ml/min) |
|---|---|---|---|
| 0.00 | 42 | 58 | 0.9 |
| 0.50 | 42 | 58 | 0.9 |
| 11.50 | 37 | 63 | 0.9 |

TABLE 6-continued

| Time (min) | Mobile phase A (%) | Mobile phase B (%) | Flow rate (ml/min) |
|---|---|---|---|
| 11.60 | ↓ | ↓ | 0.9 |
| 12.00 | 1 | 99 | ↓ |
| 12.50 | 1 | 99 | 1.3 |
| 13.50 | 1 | 99 | 1.3 |
| 13.51 | 42 | 58 | 1.3 |
| 15.50 | 42 | 58 | 1.3 |
| 15.51 | 42 | 58 | 0.9 |
| 16.00 | 42 | 58 | 0.9 |

MS Condition

MS/MS: Qtrap 6500 (manufactured by AB Sciex)
Ionization method: ESI method
Ion polarity: Positive
Measurement ion: shown in the following Table 7

TABLE 7

| Measuring object | Precursor ion [M + H]$^+$(m/z) | Product ion (m/z) | DP (V) | CE (eV) | CXP |
|---|---|---|---|---|---|
| Testosterone B | 289.2 | 97.0 | 80 | 26 | 11 |
| Testosterone-d$_3$ | 292.1 | 96.8 | 150 | 27 | 12 |

The obtained plasma testosterone concentration was analyzed by a pharmacokinetic analysis software (Phoenix WinNonlin Version 6.4: manufactured by Certara GK) to calculate a maximum plasma concentration ($C_{max}$), an area under the plasma concentration-time curve to 12 hours after administration ($AUC_{0-12\ hr}$), an area under the plasma concentration-time curve to the time of the last quantifiable measurement (or an area under the plasma concentration-time curve to the time of the last measurement at which the measurement value was not less than the quantitative lower limit) ($AUC_{0-t}$), an area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-\infty}$).

Table 8 shows the pharmacokinetic parameters results of the obtained preparations. The plasma testosterone concentration profile is shown in FIG. 2.

TABLE 8

| | $T_{max}$ (hr) | $C_{max}$ (ng/ml) | $AUC_{0-t}$ (ng · hr/ml) | $AUC_{0-\infty}$ (ng · hr/ml) | $t_{1/2}$ (hr) | $MRT_{0-\infty}$ (hr) |
|---|---|---|---|---|---|---|
| Example 1 | 1.00 | 4.96 | 37.80 | 43.77 | 8.18 | 10.75 |
| Example 2 | 0.33 | 10.45 | 54.64 | 57.82 | 5.62 | 6.33 |
| Reference Example 3 | 0.38 | 32.25 | 78.59 | 79.03 | 1.26 | 2.77 |

As apparent from the results shown in Table 8 and FIG. 2, Reference Example 3 using the testosterone with less than 50 μm shows a maximum plasma concentration ($C_{max}$) exceeding 15 ng/ml that is a criterion by FDA, while Examples 1 to 2 using the testosterone with a large particle size show a maximum plasma concentration ($C_{max}$) maintained to not more than 15 ng/ml that is a criterion by FDA. Moreover, Examples 1 to 1 show a low maximum plasma concentration ($C_{max}$), a drastically prolonged elimination half-life of plasma concentration ($t_{1/2}$), and a drastically prolonged mean residence time in plasma ($MRT_{0-\infty}$) compared with Reference Example 3, and thus enable administration twice per day. This leads to an improved medication compliance.

Moreover, when the average plasma concentration ($C_{avg}$) was estimated as $AUC_{(0-12\ hr)}/12$ on the assumption of administration twice per day (administration every 12 hours), Examples 1 to 2 show an average plasma concentration ($C_{avg}$) within the normal range, 2.01 ng/ml to 7.5 ng/ml, as shown in Table 9 below.

TABLE 9

| | Example 1 | | | Example 2 | | |
|---|---|---|---|---|---|---|
| No. | 1 | 2 | 3 | 1 | 2 | 3 |
| $C_{avg}$ | 2.50 | 2.36 | 2.13 | 4.36 | 2.86 | 3.33 |
| Average of $C_{avg}$ | | 2.33 | | | 3.51 | |

Examples 3 to 5 and Reference Example 4

(1) Formulation of Preparation

The formulations of preparations of Example 3 to 5 and Reference Example 4 are shown in Table 10 below.

TABLE 10

| Ingredient (average particle size) | Example 3 | Example 4 | Example 5 | Reference Example 4 |
|---|---|---|---|---|
| Testosterone C (classification 273 μm) | 2 mg | — | — | — |
| Testosterone C classified product (131 μm) | — | 2 mg | — | — |
| Testosterone C classified product (70.4 μm) | — | — | 2 mg | — |
| Testosterone C pulverized product (16.2 μm) | — | — | — | 2 mg |
| Lactose | 18 mg | 18 mg | 18 mg | 18 mg |

(2) Formulation Process

To a classified product of Testosterone C or a pulverized product thereof [a classified product which was classified by sieving Testosterone C and of which the volume average particle size was measured after classification (a volume average particle size of 273 μm: Example 3, 131 μm: Example 4, 70.4 μm: Example 5), and a pulverized product which was obtained by pulverizing Testosterone C in a mortar and of which the volume Average particle size was measured after pulverization (a volume average particle size of 16.2 μm: Reference Example 4)] was added and mixed lactose. The mixture was filled into a cylindrical device to give a preparation for administration.

(3) Pharmacokinetic Evaluation

For each one of aged male dogs (eight dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of analysis. The plasma testosterone concentration was measured under the following analysis conditions.

HPLC Condition

HPLC: 2795 (manufactured by Waters corporation)
Column: Chromolith Performance RP-18e (3.0 mmi.d.× 100 mm, manufactured by Merck KGaA)
Mobile phase A: 0.005 mol/l ammonium acetate solution
Mobile phase B: methanol
Column temperature: 45° C.
Temperature in sample chamber: 10° C.
Injection volume: 10 μL
Gradient condition: shown in the following Table 11

TABLE 11

| Time (min) | Mobile phase A (%) | Mobile phase B (%) | Flow rate (ml/min) | Curve |
|---|---|---|---|---|
| 0.00 | 40 | 60 | 0.40 | 1 |
| 1.00 | 40 | 60 | 0.40 | 1 |
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive
Measurement ion: shown in the following Table 12

TABLE 12

| Measuring object | Precursor ion $[M + H]^+$ (m/z) | Product ion (m/z) | Cone (V) | Col (eV) |
|---|---|---|---|---|
| Testosterone C | 289.3 | 97.0 | 50 | 18 |
| Testosterone-$d_3$ | 292.3 | 97.0 | 35 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10\ hr}$), an area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 13 shows the pharmacokinetic parameters of the obtained preparations. The plasma testosterone concentration profile is shown in FIG. 3. The value represents the mean and the standard deviation (the same applies hereinafter).

TABLE 13

| | T (D50) | $T_{max}$ (hr) | $C_{max}$ (ng/ml) | $AUC_{0-10hr}$ (ng·hr/mL) | $AUC_{0-\infty}$ (ng·hr/mL) | $t_{1/2}$ (hr) | $MRT_{0-10hr}$ (hr) | $MRT_{0-\infty}$ (hr) |
|---|---|---|---|---|---|---|---|---|
| Example 3 | 273 μm | 0.56 ± 0.29 | 3.354 ± 1.138 | 10.159 ± 1.953 | 17.380 ± 12.651 | 4.65 ± 3.92 | 3.06 ± 0.93 | 7.76 ± 7.11 |
| Example 4 | 131 μm | 0.69 ± 0.62 | 4.121 ± 1.590 | 12.634 ± 5.766 | 15.789 ± 6.626 | 2.97 ± 1.33 | 2.79 ± 0.54 | 5.17 ± 2.32 |
| Example 5 | 70.4 μm | 0.81 ± 0.76 | 10.419 ± 3.433 | 26.289 ± 8.658 | 28.486 ± 8.712 | 2.30 ± 0.92 | 2.26 ± 0.39 | 3.18 ± 1.76 |
| Reference Example 4 | 16.2 μm | 0.31 ± 0.12 | 19.639 ± 6.425 | 39.614 ± 13.009 | 41.080 ± 12.624 | 1.52 ± 0.42 | 1.77 ± 0.19 | 2.20 ± 0.71 |

As apparent from the results shown in Table 13 and FIG. 3, Reference Example 4 using the testosterone with less than 50 μm shows a maximum plasma concentration ($C_{max}$) exceeding 15 ng/ml that is a criterion by FDA, while Examples 3 to 5 using the testosterone with a large particle size show a maximum plasma concentration ($C_{max}$) maintained to not more than 15 ng/ml that is a criterion by FDA.

Examples 6 to 9

(1) Formulation of Preparation

The formulations of preparations of Examples 6 to 8 are shown in Table 14 below.

TABLE 14

| Ingredient (average particle size) | Example 6 | Example 7 | Example 8 |
|---|---|---|---|
| Testosterone C classified product (114 μm) | 2 mg | 2 mg | 2 mg |
| Hydroxypropylcellulose H | 18 mg | — | — |
| Hydroxypropylcellulose M | — | 18 mg | — |
| Hydroxypropylcellulose L | — | — | 18 mg |

(2) Formulation Process

To a classified product of Testosterone C [a classified product which was classified by sieving Testosterone C and of which the volume average particle size was measured after classification (a volume average particle size of 114 μm)] was added and mixed hydroxypropylcellulose. The mixture was filled into a cylindrical device to give a preparation for administration.

(3) Pharmacokinetic Evaluation

For each one of aged male dogs (eight dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a syringe. The blood collection volume was about 1 ml per point of time. The collected blood was immediately transferred in a vacuum plasma collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: 2795 (manufactured by Waters corporation)

Column: Chromolith Performance RP-18e (3.0 mmi.d.× 100 mm, manufactured by Merck KGaA)

Mobile phase A: 0.005 mol/l ammonium acetate aqueous solution

Mobile phase B: methanol

Column temperature: 45° C.

Temperature in sample chamber: 10° C.

Injection volume: 10 μL

Gradient condition: shown in the following Table 15

TABLE 15

| Time (min) | Mobile phase A (%) | Mobile phase B (%) | Flow rate (ml/min) | Curve |
|---|---|---|---|---|
| 0.00 | 40 | 60 | 0.40 | 1 |
| 1.00 | 40 | 60 | 0.40 | 1 |
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive Measurement ion: shown in the following Table 16

TABLE 16

| Measuring object | Precursor ion $[M+H]^+$ (m/z) | Product ion (m/z) | Cone (V) | Col (eV) |
|---|---|---|---|---|
| Testosterone C | 289.3 | 97.0 | 50 | 18 |
| Testosterone-$d_3$ | 292.3 | 97.0 | 30 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10\ hr}$), an area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 17 shows the pharmacokinetic parameters of the obtained preparations. The plasma testosterone concentration profile is shown in FIG. 4.

TABLE 17

| | Water-soluble polymer | $T_{max}$ (hr) | $C_{max}$ (ng/ml) | $AUC_{0-10hr}$ (ng·hr/mL) | $AUC_{0-\infty}$ (ng·hr/mL) | $t_{1/2}$ (hr) | $MRT_{0-10hr}$ (hr) | $MRT_{0-\infty}$ (hr) | $C_{avg}$ (ng/ml) |
|---|---|---|---|---|---|---|---|---|---|
| Example 6 | HPC-H | 0.66 ± 0.60 | 8.576 ± 3.070 | 34.318 ± 10.251 | 47.809 ± 13.742 | 5.33 ± 2.83 | 3.50 ± 0.48 | 7.74 ± 3.92 | 3.432 ± 1.025 |
| Example 7 | HPC-M | 0.84 ± 0.55 | 7.585 ± 2.041 | 32.737 ± 10.193 | 55.369 ± 34.732 | 7.37 ± 4.96 | 3.53 ± 0.41 | 10.19 ± 6.36 | 3.274 ± 1.019 |
| Example 8 | HPC-L | 0.94 ± 1.26 | 9.372 ± 3.489 | 34.994 ± 9.333 | 38.854 ± 12.438 | 2.37 ± 1.02 | 2.89 ± 0.52 | 3.85 ± 1.37 | 3.499 ± 0.933 |

As apparent from the results shown in Table 17 and FIG. 4, Examples 6 to 8 using the testosterone having a volume average particle size of 114 μm and the water-soluble polymer in combination show a maximum plasma concentration ($C_{max}$) maintained to not more than 15 ng/ml that is a criterion by FDA and show an average plasma concentration ($C_{avg}$) within the range from 2.01 ng/ml to 7.5 ng/ml.

Examples 9 to 12

(1) Formulation of Preparation

The formulations of preparations of Examples 9 to 12 are shown in Table 18 below.

TABLE 18

| Ingredient (average particle size) | Example 9 | Example 10 | Example 11 | Example 12 |
|---|---|---|---|---|
| Testosterone C classified product (114 μm) | 2 mg | 2 mg | 2 mg | 2 mg |
| Hydroxypropylcellulose M | 2 mg | 6 mg | 10 mg | 14 mg |
| Lactose | 16 mg | 12 mg | 8 mg | 4 mg |

(2) Formulation Process

To a classified product of Testosterone C [a Classified product which was classified by sieving Testosterone C and of which the average particle size was measured after classification (an average particle size of 114 μm)] was added and mixed Hydroxypropylcellulose M and lactose. The mixture was filled into a cylindrical device to give a preparation for administration.

(3) Pharmacokinetic Evaluation

For each one of aged male dogs (seven dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a heparin-treated syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: 2795 (manufactured by Waters corporation)
Column: Chromolith Performance RP-18e (3.0 mmi.d.× 100 mm, manufactured by Merck KGaA)
Mobile phase A: 0.005 mol/l ammonium acetate solution
Mobile phase B: methanol
Column temperature: 45° C.
Temperature in sample chamber: 10° C.
Injection volume: 10 μL
Gradient condition: shown in the following Table 19

TABLE 19

| Time (min) | Mobile phase A (%) | Mobile phase B (%) | Flow rate (ml/min) | Curve |
|---|---|---|---|---|
| 0.00 | 40 | 60 | 0.40 | 1 |
| 1.00 | 40 | 60 | 0.40 | 1 |

TABLE 19-continued

| Time (min) | Mobile phase A (%) | Mobile phase B (%) | Flow rate (ml/min) | Curve |
|---|---|---|---|---|
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive
Measurement ion: shown in the following Table 20

TABLE 20

| Measuring object | Precursor ion $[M + H]^+$(m/z) | Product ion (m/z) | Cone (V) | Col (eV) |
|---|---|---|---|---|
| Testosterone C | 289.3 | 97.0 | 50 | 18 |
| Testosterone-$d_3$ | 292.3 | 97.0 | 35 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10\ hr}$), an area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 21 shows the pharmacokinetic parameters of the obtained preparations. The plasma testosterone concentration profile is shown in FIG. 5.

TABLE 21

| | Added amount of HPC-M | $T_{max}$ (hr) | $C_{max}$ (ng/ml) | $AUC_{0-10hr}$ (ng · hr/mL) | $AUC_{0-\infty}$ (ng · hr/mL) | $t_{1/2}$ (hr) | $MRT_{0-10hr}$ (hr) | $MRT_{0-\infty}$ (hr) | $C_{avg}$ (ng/ml) |
|---|---|---|---|---|---|---|---|---|---|
| Example 9 | 2 mg | 0.43 ± 0.28 | 8.983 ± 4.408 | 22.656 ± 11.483 | 29.327 ± 12.795 | 3.77 ± 1.86 | 2.69 ± 0.61 | 5.62 ± 3.20 | 2.266 ± 1.148 |
| Example 10 | 6 mg | 0.57 ± 0.31 | 6.885 ± 2.236 | 20.773 ± 5.245 | 23.090 ± 6.902 | 2.39 ± 0.97 | 2.44 ± 0.40 | 3.46 ± 1.35 | 2.077 ± 0.525 |
| Example 11 | | 0.54 ± 0.65 | 7.664 ± 2.802 | 24.736 ± 8.362 | 29.168 ± 11.751 | 2.66 ± 1.05 | 2.81 ± 0.59 | 4.28 ± 1.86 | 2.474 ± 0.836 |
| Example 12 | 14 mg | 0.50 ± 0.35 | 7.563 ± 2.617 | 27.928 ± 8.920 | 31.688 ± 10.827 | 3.07 ± 0.64 | 3.28 ± 0.34 | 4.56 ± 0.99 | 2.793 ± 0.892 |

An apparent from the results shown in Table 21 and FIG. 5, all examples for the added amounts show a maximum plasma concentration ($C_{max}$) maintained to not more than 15 ng/ml that is a criterion by FDA and show an average plasma concentration ($C_{avg}$) within the range from 2.01 ng/ml to 7.5 ng/ml.

Examples 13 to 15

(1) Formulation of Preparation

The formulations of preparations of Examples 13 to 15 are shown in Table 22 below.

TABLE 22

| Ingredient (average particle size) | Example 13 | Example 14 | Example 15 |
|---|---|---|---|
| Testosterone C classified product (114 μm) | 2 mg | 2 mg | 2 mg |
| Hydroxypropylcellulose M | 8 mg | — | — |
| Hydroxypropylcellulose H | — | 8 mg | 8 mg |
| Lactose | — | — | 10 mg |

(2) Formulation Process

To a classified product of Testosterone C [a classified product which was classified by sieving Testosterone C and of which the average particle size was measured after classification (an average particle size of 114 μm)] was added and mixed hydroxypropylcellulose and/or lactose at the proportion shown in Table 22. The mixture was filled into a cylindrical device to give a preparation for administration.

(3) Pharmacokinetic Evaluation

For each one of aged male dogs (seven dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: 2795 (manufactured by Waters corporation)
Column: Chromolith Performance RP-18e (3.0 mmi.d.× 100 mm, manufactured by Merck KGaA)
Mobile phase A: 0.005 mol/l ammonium acetate solution
Mobile phase B: methanol
Column temperature: 45° C.
Temperature in sample chamber: 10° C.
Injection volume: 10 μL
Gradient condition: shown in the following Table 23

TABLE 23

| Time (min) | Mobile phase A (%) | Mobile phase B (%) | Flow rate (ml/min) | Curve |
|---|---|---|---|---|
| 0.00 | 40 | 60 | 0.40 | 1 |
| 1.00 | 40 | 60 | 0.40 | 1 |
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive
Measurement ion: shown in the following Table 24

TABLE 24

| Measuring object | Precursor ion $[M + H]^+$ (m/z) | Product ion (m/z) | Cone (V) | Col (eV) |
|---|---|---|---|---|
| Testosterone C | 289.3 | 97.0 | 50 | 18 |
| Testosterone-$d_3$ | 292.3 | 97.0 | 50 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10\ hr}$), area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 25 shows the pharmacokinetic parameters of the obtained preparations for administration. The plasma testosterone concentration profile is shown in FIG. 6.

TABLE 25

| | $T_{max}$ (hr) | $C_{max}$ (ng/ml) | $AUC_{0-10hr}$ (ng·hr/mL) | $AUC_{0-\infty}$ (ng·hr/mL) | $t_{1/2}$ (hr) | $MRT_{0-10hr}$ (hr) | $MRT_{0-\infty}$ (hr) | $C_{avg}$ (ng/ml) |
|---|---|---|---|---|---|---|---|---|
| Example 13 | 0.68 ± 0.64 | 7.528 ± 1.488 | 30.786 ± 6.932 | 46.600 ± 26.594 | 5.03 ± 3.41 | 3.41 ± 0.54 | 7.55 ± 5.30 | 3.079 ± 0.693 |
| Example 14 | 0.57 ± 0.64 | 8.870 ± 3.028 | 30.160 ± 7.226 | 39.179 ± 13.307 | 4.09 ± 1.73 | 3.27 ± 0.43 | 5.93 ± 3.11 | 3.016 ± 0.723 |
| Example 15 | 0.61 ± 0.67 | 9.516 ± 2.666 | 34.054 ± 5.918 | 38.113 ± 8.676 | 3.10 ± 2.21 | 2.87 ± 0.37 | 4.11 ± 1.00 | 3.405 ± 0.592 |

As apparent from the results shown in Table 25 and FIG. 6, all examples show a maximum plasma concentration ($C_{max}$) maintained to not more than 15 ng/ml that is a criterion by FDA and shew an average plasma concentration ($C_{avg}$) within the range from 2.01 ng/ml to 7.5 ng/ml.

Examples 16 to 21

(1) Formulation of Preparation

The formulations of preparations of Examples 16 to 21 are shown in Table 26 below.

TABLE 26

| Ingredient (average particle size) | Example 16 | Example 17 | Example 18 | Example 19 | Example 20 | Example 21 |
| --- | --- | --- | --- | --- | --- | --- |
| Testosterone C. classified product (114 μm) | 2 mg | 2 mg | 2 mg | 2 mg | 2 mg | 2 mg |
| Pregelatinized starch | 8 mg | — | — | — | — | — |
| Carboxyvinylpolymer | — | 8 mg | — | — | — | — |
| Sodium alginate | — | — | 8 mg | — | — | — |
| Hydroxypropylmethylcellulose | — | — | — | 8 mg | — | — |
| Polyvinylpyrrolidone | — | — | — | — | 8 mg | — |
| Xanthan gum | — | — | — | — | — | 8 mg |

(2) Formulation Process

To 2 mg of a classified product of Testosterone C [a classified product which was classified by sieving Testosterone C and of which the average particle size was measured after classification (an average particle size of 114 μm)] was added and mixed 8 mg of a water-soluble polymer shown in Table 26. The mixture was filled into a cylindrical device to give a preparation for administration.

(3) Pharmacokinetic Evaluation

For each one of aged male dogs (seven dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: 2795 (manufactured by Waters corporation)
Column: Chromolith Performance RP-18e (3.0 mmi.d.× 100 mm, manufactured by Merck KGaA)
  Mobile phase A: 0.005 mol/l ammonium acetate solution
  Mobile phase B: methanol
  Column temperature: 45° C.
  Temperature in sample chamber: 10° C.
  Injection volume: 10 μL
  Gradient condition: shown in the following Table 27

TABLE 27

| Time (min) | Mobile phase A (%) | Mobile phase B (%) | Flow rate (ml/min) | Curve |
| --- | --- | --- | --- | --- |
| 0.00 | 40 | 60 | 0.40 | 1 |
| 1.00 | 40 | 60 | 0.40 | 1 |
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive
Measurement ion: shown in the following Table 28

TABLE 28

| Measuring object | Precursor ion $[M + H]^+$ (m/z) | Product ion (m/z) | Cone (V) | Col (eV) |
| --- | --- | --- | --- | --- |
| Testosterone C | 289.3 | 97.0 | 50 | 18 |
| Testosterone-$d_3$ | 292.3 | 97.0 | 35 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10\ hr}$), area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 29 shows the pharmacokinetic parameters of the obtained preparations for administration. The plasma testosterone concentration profile is shown in FIG. 7.

TABLE 29

| | $T_{max}$ (hr) | $C_{max}$ (ng/ml) | $AUC_{0-10hr}$ (ng·hr/mL) | $AUC_{0-\infty}$ (ng·hr/mL) | $t_{1/2}$ (hr) | $MRT_{0-10hr}$ (hr) | $MRT_{0-\infty}$ (hr) | $C_{avg}$ (ng/ml) |
|---|---|---|---|---|---|---|---|---|
| Example 16 | 0.82 ± 0.81 | 8.223 ± 3.444 | 26.705 ± 9.659 | 33.250 ± 20.286 | 4.07 ± 5.05 | 2.51 ± 0.30 | 5.04 ± 4.39 | 2.671 ± 0.966 |
| Example 17 | 0.96 ± 0.74 | 8.740 ± 2.329 | 30.036 ± 6.828 | 45.663 ± 14.155 | 7.72 ± 10.16 | 3.13 ± 0.60 | 10.86 ± 12.09 | 3.004 ± 0.683 |
| Example 18 | 0.54 ± 0.65 | 8.430 ± 2.068 | 29.675 ± 11.078 | 36.124 ± 17.529 | 3.56 ± 1.06 | 3.04 ± 0.48 | 4.90 ± 1.54 | 2.968 ± 1.108 |
| Example 19 | 0.29 ± 0.09 | 8.490 ± 3.198 | 35.202 ± 12.148 | 46.203 ± 16.777 | 4.25 ± 1.30 | 3.41 ± 0.66 | 6.40 ± 2.04 | 3.520 ± 1.215 |
| Example 20 | 0.86 ± 0.83 | 7.078 ± 2.064 | 22.590 ± 8.900 | 31.208 ± 14.526 | 4.64 ± 3.34 | 2.65 ± 0.73 | 6.37 ± 4.13 | 2.259 ± 0.890 |
| Example 21 | 0.64 ± 0.66 | 9.789 ± 4.048 | 35.424 ± 17.330 | 41.866 ± 24.633 | 2.78 ± 0.81 | 2.93 ± 0.45 | 3.95 ± 1.36 | 3.542 ± 1.733 |

As apparent from the results shown in Table 29 and FIG. 7, all examples show a maximum plasma concentration ($C_{max}$) maintained to not more than 15 ng/ml that is a criterion by FDA and show an average plasma concentration ($C_{avg}$) within the range from 2.01 ng/ml to 7.5 ng/ml.

Examples 22 to 27

(1) Formulation of Preparation

The formulations of preparations of Examples 22 to 27 are shown in Table 30 below.

TABLE 30

| Ingredient (average particle size) | Example 22 | Example 23 | Example 24 | Example 25 | Example 26 | Example 27 |
|---|---|---|---|---|---|---|
| Testosterone C. classified product (114 μm) | 2 mg | 2 mg | 2 mg | 2 mg | 2 mg | 2 mg |
| Polyethylene glycol | 8 mg | — | — | — | — | — |
| Polyvinyl alcohol | — | 8 mg | — | — | — | — |
| Chitosan | — | — | 8 mg | — | — | — |
| Carmellose sodium | — | — | — | 8 mg | — | — |
| Locust bean gum | — | — | — | — | 8 mg | — |
| Copolyvidone | — | — | — | — | — | 8 mg |

(2) Formulation Process

To 2 mg of a pulverized product of Testosterone C [a classified product which was obtained by pulverizing Testosterone C in a mortar and of which the volume average particle size was measured after pulverization (a volume average particle size of 114 μm)] was added and mixed 8 mg of a water-soluble polymer shown in Table 30. The mixture was filled into a cylindrical device to give a preparation for administration.

(3) Pharmacokinetic Evaluation

For each one of aged male dogs (seven dogs), a cylindrical device filled with the preparation was inserted 1 cm into one of the nasal cavities, and a single nasal dose was administered (the amount of testosterone administered: 2 mg). At 0.25, 0.5, 1, 2, 4, 6, 8, 10, and 24 hours after the nasal administration, the blood was collected using a 23G needle and a syringe. The blood collection volume was about 1 ml per point of time. The collected blood was immediately transferred in a vacuum blood collection tube with heparin sodium and was stirred lightly. After centrifugation (3000 rpm, 10 minutes, 4° C.), the plasma was collected and was cryopreserved until the time of measurement. The plasma testosterone concentration was measured under the following analysis conditions.

HPLC Condition

HPLC: 2795 (manufactured by Waters corporation)
Column: Chromolith Performance RP-18e (3.0 mmi.d.× 100 mm, manufactured by Merck KGaA)
Mobile phase A: 0.005 mol/l ammonium acetate solution
Mobile phase B: methanol
Column temperature: 45° C.
Temperature in sample chamber: 10° C.
Injection volume: 10 μL
Gradient condition: shown in the following Table 31

TABLE 31

| Time (min) | Mobile phase A (%) | Mobile phase B (%) | Flow rate (ml/min) | Curve |
|---|---|---|---|---|
| 0.00 | 40 | 60 | 0.40 | 1 |
| 1.00 | 40 | 60 | 0.40 | 1 |
| 4.00 | 20 | 80 | 0.40 | 6 |
| 6.00 | 10 | 90 | 0.40 | 6 |
| 6.50 | 5 | 95 | 0.90 | 11 |
| 8.50 | 40 | 60 | 0.40 | 11 |

MS Condition

MS/MS: Quattro ultima (manufactured by Waters corporation)
Ionization method: ESI method
Ion polarity: Positive
Measurement ion: shown in the following Table 32

TABLE 32

| Measuring object | Precursor ion $[M + H]^+$ (m/z) | Product ion (m/z) | Cone (V) | Col (eV) |
|---|---|---|---|---|
| Testosterone C | 289.3 | 97.0 | 50 | 18 |
| Testosterone-$d_3$ | 292.3 | 97.0 | 35 | 15 |

The obtained plasma testosterone concentration was analyzed by a pharmacokinetic analysis software (Phoenix WinNonlin Version 7.0: manufactured by Certara GK) to calculate a maximum plasma concentration ($C_{max}$), an area under the plasma concentration-time curve to 10 hours after administration ($AUC_{0-10}$ hr), an area under the plasma concentration-time curve extrapolated to infinity ($AUC_{0-\infty}$), a time to reach a maximum plasma concentration ($T_{max}$), an elimination half-life ($t_{1/2}$), and a mean residence time in plasma ($MRT_{0-10\ hr}$ and $MRT_{0-\infty}$). Moreover, the average plasma concentration ($C_{avg}$) was estimated as $AUC_{(0-10\ hr)}/10$ on the assumption of administration twice per day (administration every 10 hours).

Table 33 shows the pharmacokinetic parameters of the obtained preparations for administration. The plasma testosterone concentration profile is shown in FIG. 8.

TABLE 33

| | $T_{max}$ (hr) | $C_{max}$ (ng/ml) | $AUC_{0-10hr}$ (ng·hr/mL) | $AUC_{0-\infty}$ (ng·hr/mL) | $t_{1/2}$ (hr) | $MRT_{0-10hr}$ (hr) | $MRT_{0-\infty}$ (hr) | $C_{avg}$ (ng/ml) |
|---|---|---|---|---|---|---|---|---|
| Example 22 | 0.64 ± 0.66 | 6.858 ± 2.321 | 20.259 ± 4.088 | 38.036 ± 12.818 | 8.75 ± 7.64 | 3.11 ± 0.61 | 13.05 ± 10.21 | 2.026 ± 0.409 |
| Example 23 | 0.39 ± 0.28 | 6.278 ± 2.156 | 20.113 ± 3.929 | 33.687 ± 14.263 | 6.35 ± 5.44 | 3.15 ± 0.66 | 9.86 ± 8.02 | 2.011 ± 0.393 |
| Example 24 | 0.54 ± 0.65 | 8.982 ± 2.981 | 29.488 ± 5.917 | 35.591 ± 10.257 | 3.07 ± 0.70 | 3.11 ± 0.44 | 4.90 ± 1.40 | 2.949 ± 0.592 |
| Example 25 | 0.71 ± 0.67 | 7.649 ± 2.372 | 24.258 ± 7.218 | 30.129 ± 9.260 | 3.42 ± 2.11 | 2.60 ± 0.52 | 5.07 ± 2.42 | 2.426 ± 0.722 |
| Example 26 | 0.64 ± 0.66 | 6.814 ± 2.404 | 23.934 ± 5.193 | 29.718 ± 7.382 | 3.16 ± 0.88 | 3.10 ± 0.37 | 5.29 ± 2.11 | 2.393 ± 0.519 |
| Example 27 | 0.86 ± 0.83 | 7.579 ± 2.486 | 19.723 ± 4.819 | 24.034 ± 5.097 | 5.08 ± 4.61 | 2.72 ± 0.61 | 6.37 ± 4.54 | 1.972 ± 0.482 |

As apparent from the results shown in Table 33 and FIG. 8, all examples show a maximum plasma concentration ($C_{max}$) maintained to not more than 15 ng/ml that is a criterion by FDA, and Examples 22 to 26 show an average plasma concentration ($C_{avg}$) within the range from 2.01 ng/ml to 7.5 ng/ml. Whereas, Example 27 shows an average plasma concentration ($C_{avg}$) less than 2.01 ng/ml, probably because of a low viscosity of the water-soluble polymer.

INDUSTRIAL APPLICABILITY

The powder preparation for nasal administration of the present invention can be used as various therapeutic agents utilizing the steroid hormones (e.g., a therapeutic agent for late-onset hypogonadism, an anticancer agent, a therapeutic agent for menopausal disorder, a therapeutic agent for osteoporosis, a therapeutic agent for chronic kidney disease, a therapeutic agent for infertility, a therapeutic agent for menstrual disorder, a contraceptive, a therapeutic agent for functional uterine bleeding, and a therapeutic agent for endometriosis). In particular, the powder preparation containing testosterone as the steroid hormones can be used effectively as a therapeutic agent for late-onset hypogonadism.

The invention claimed is:

1. A powder preparation for nasal administration, comprising:
   (i) a particulate of a steroid hormone testosterone or a derivative thereof as an active ingredient, wherein said particulate has a volume average particle size (D50) of 50 μm to 300 μm as measured by a laser diffraction, and wherein the particle size of each particle is an average of a major axis and a minor axis; and
   (ii) a water-soluble polymer; and
   wherein said powder preparation controls an average blood concentration of the steroid hormone over 12 hours in an adult male to be from 2 ng/ml to 7.5 ng/ml.

2. The powder preparation for nasal administration according to claim 1, wherein the water-soluble polymer is a water-soluble polysaccharide or a combination of water-soluble polysaccharides.

3. The powder preparation for nasal administration according to claim 2, wherein the water-soluble polysaccharide or the combination of water-soluble polysaccharides comprise a cellulose having hydroxyalkyl groups.

4. The powder preparation for nasal administration according to claim 1, wherein the water-soluble polymer is free from a crystalline cellulose and a carboxymethylcellulose sodium.

5. The powder preparation for nasal administration according to claim 1, wherein the water-soluble polymer forms a particulate having a volume average particle size (D50) of 10-500 μm.

6. The powder preparation for nasal administration according to claim 1, wherein a weight ratio of the water-soluble polymer to the particulate of the steroid hormone is 1:50.

7. The powder preparation for nasal administration according to claim 1, providing a maximum plasma concentration of the steroid hormones in an adult male to be not more than 15 ng/ml.

* * * * *